(12) United States Patent
Schmid et al.

(10) Patent No.: US 11,357,615 B2
(45) Date of Patent: Jun. 14, 2022

(54) APPARATUS FOR MAKING AN EYE IMPLANT

(71) Applicant: Alcon Inc., Fribourg (CH)

(72) Inventors: Stefan Schmid, Neuendettelsau (DE); Stefan Bornemann, Nuremberg (DE); Thomas Deisinger, Cadolzburg (DE)

(73) Assignee: Alcon Inc., Fribourg (CH)

( * ) Notice: Subject to any disclaimer, the term of this patent is extended or adjusted under 35 U.S.C. 154(b) by 455 days.

(21) Appl. No.: 16/383,007

(22) Filed: Apr. 12, 2019

(65) Prior Publication Data
US 2019/0314145 A1 Oct. 17, 2019

Related U.S. Application Data

(60) Provisional application No. 62/658,841, filed on Apr. 17, 2018.

(51) Int. Cl.
*B29C 41/20* (2006.01)
*B29C 41/22* (2006.01)
(Continued)

(52) U.S. Cl.
CPC .............. *A61F 2/14* (2013.01); *B29C 64/209* (2017.08); *B29C 64/264* (2017.08);
(Continued)

(58) Field of Classification Search
CPC ......... A61F 2240/001; A61F 2240/002; B29C 2035/0838; B29C 59/16; B29C 64/209; B29C 64/264; B29C 64/268; B29C 64/386; B29C 64/393; B29C 69/001; B29C 71/04; B29C 41/20; B29C 41/22; B29C 70/68; B29C 70/681; B29C 70/78; B29D 11/023; B33Y 30/00; B33Y 50/00; B33Y 50/02; G01N 2021/8411; G01N 2021/8416; G05B 19/4099; G06T 2207/10021; G06T 2207/10101
(Continued)

(56) References Cited

U.S. PATENT DOCUMENTS

2015/0165683 A1* 6/2015 Ch .................. B29C 64/393
382/141
2015/0197063 A1 7/2015 Shinar et al.
(Continued)

FOREIGN PATENT DOCUMENTS

EP 3208077 A1 8/2017
WO 2016115369 A1 7/2016

*Primary Examiner* — Leo B Tentoni

(57) ABSTRACT

In certain embodiments, a system for making an implant for an eye comprises a printer, a camera, and a computer. The printer prints material onto a target and has a printer head and printer controller. The printer head deposits the material onto the target, and the printer controller moves the printer head to deposit the material onto a specific location of the target. The camera generates an image to monitor the printing of the material. The computer stores a pattern for the implant, which is designed to provide refractive treatment for the eye; sends instructions to the printer controller to move the printer head to print the material onto the target according to the pattern; assesses the image from the camera according to the pattern; and adjusts the instructions in response to the image.

13 Claims, 4 Drawing Sheets

(51) Int. Cl.
| | |
|---|---|
| B29C 59/16 | (2006.01) |
| B29C 70/68 | (2006.01) |
| B29C 70/78 | (2006.01) |
| B29C 71/02 | (2006.01) |
| B33Y 30/00 | (2015.01) |
| G05B 19/4099 | (2006.01) |
| A61F 2/14 | (2006.01) |
| B29C 64/30 | (2017.01) |
| B29C 64/386 | (2017.01) |
| B33Y 50/00 | (2015.01) |
| B33Y 80/00 | (2015.01) |
| B33Y 10/00 | (2015.01) |
| B29C 64/393 | (2017.01) |
| B29C 64/209 | (2017.01) |
| B29C 64/264 | (2017.01) |
| B29C 64/268 | (2017.01) |
| B29D 11/02 | (2006.01) |
| B29C 35/08 | (2006.01) |
| G01N 21/84 | (2006.01) |

(52) U.S. Cl.
CPC ............ B29C 64/268 (2017.08); B29C 64/30 (2017.08); B29C 64/386 (2017.08); B29C 64/393 (2017.08); *B29C 70/681* (2013.01); *B29D 11/023* (2013.01); B33Y 10/00 (2014.12); B33Y 50/00 (2014.12); B33Y 80/00 (2014.12); *A61F 2240/001* (2013.01); *A61F 2240/002* (2013.01); *B29C 2035/0838* (2013.01); *G01N 2021/8411* (2013.01); *G01N 2021/8416* (2013.01); *G06T 2207/10021* (2013.01); *G06T 2207/10101* (2013.01)

(58) Field of Classification Search
USPC ....... 425/135, 145, 174.4, 375, 110; 348/86; 382/141; 700/119
See application file for complete search history.

(56) References Cited

U.S. PATENT DOCUMENTS

| | | | |
|---|---|---|---|
| 2016/0009029 A1* | 1/2016 | Cohen | B29C 64/209 264/493 |
| 2017/0087766 A1* | 3/2017 | Chung | B33Y 50/02 |
| 2018/0143147 A1* | 5/2018 | Milner | B29C 64/393 |
| 2019/0240070 A1 | 8/2019 | Schmid et al. | |
| 2020/0069466 A1 | 3/2020 | Bomemann | |

* cited by examiner

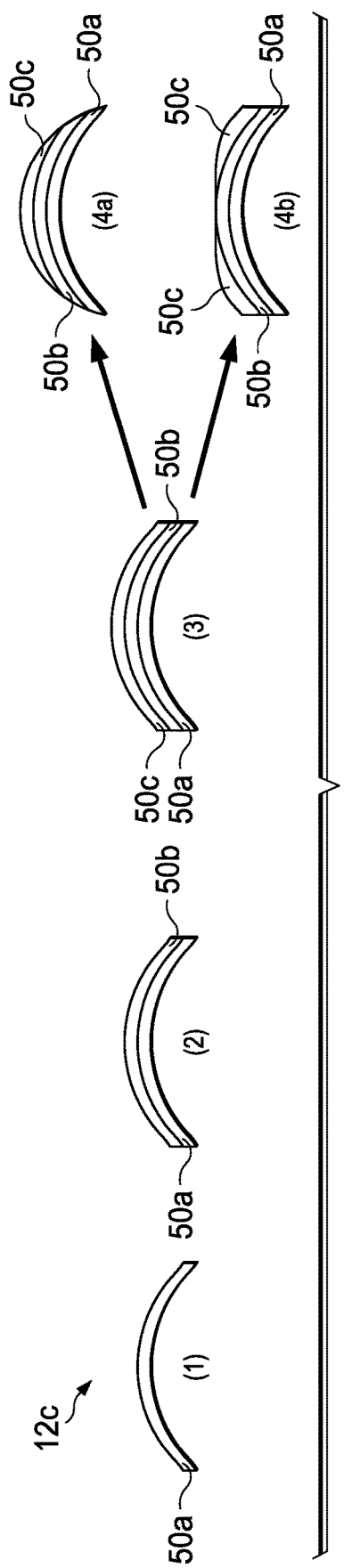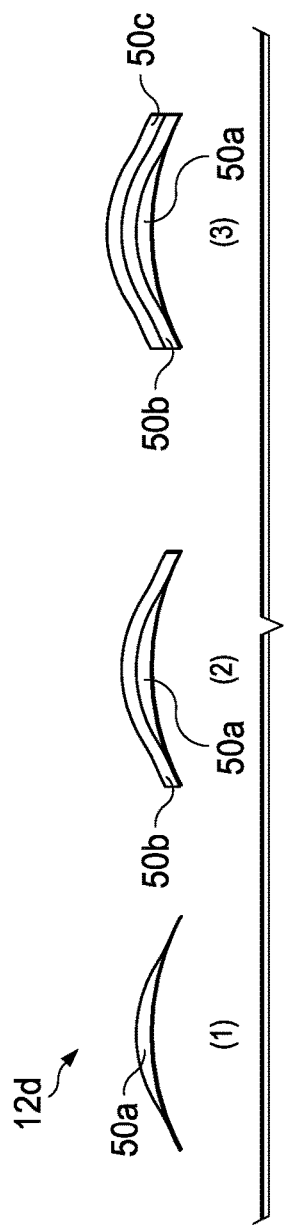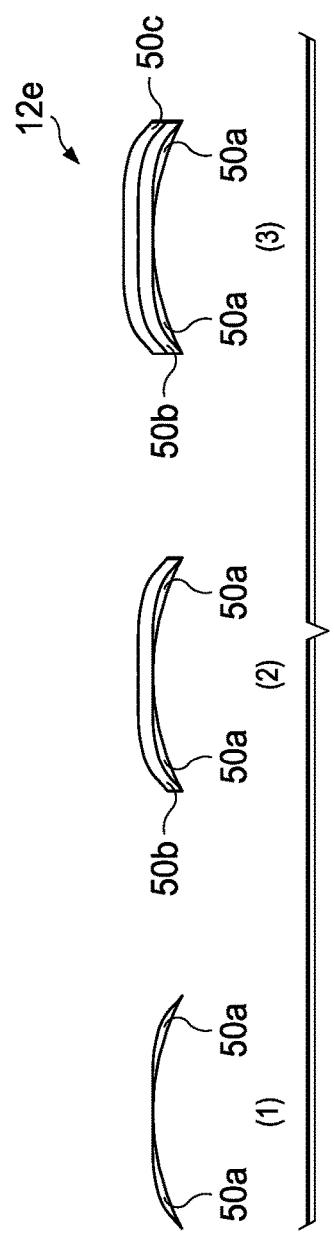
FIG. 4A
FIG. 4B
FIG. 4C

APPARATUS FOR MAKING AN EYE IMPLANT

TECHNICAL FIELD

The present disclosure relates generally to refractive treatment of an eye, and more specifically to making an implant for an eye.

BACKGROUND

Refractive treatment of an eye refers to techniques performed to change the refractive properties of the eye to reduce refractive error to improve vision. Refractive error occurs when parts of the eye do not bend light correctly, resulting in a blurred image. The main types of refractive errors are myopia (nearsightedness), hyperopia (farsightedness), presbyopia (loss of near vision with age), and astigmatism. Ocular implants are used in one type of refractive treatment. An ocular implant is implanted into the eye to change the refractive properties to improve vision.

BRIEF SUMMARY

In certain embodiments, a system for making an implant for an eye comprises a printer, a camera, and a computer. The printer prints material onto a target and has a printer head and printer controller. The printer head deposits the material onto the target, and the printer controller moves the printer head to deposit the material onto a specific location of the target. The camera generates an image to monitor the printing of the material. The computer stores a pattern for the implant, which is designed to provide refractive treatment for the eye; sends instructions to the printer controller to move the printer head to print the material onto the target according to the pattern; assesses the image from the camera according to the pattern; and adjusts the instructions in response to the image.

In certain embodiments, a method for making an implant for an eye includes storing a pattern for an implant designed to provide refractive treatment for the eye. Instructions are sent to a printer controller to move a printer head to print material onto a target according to the pattern. An image is generated to monitor the printing of the material. The image is assessed according to the pattern, and adjusting the instructions are adjusted in response to the image.

BRIEF DESCRIPTION OF THE DRAWINGS

Embodiments of the present disclosure are described by way of example in greater detail with reference to the attached figures, in which:

FIGS. 4A to 4C illustrate examples of implants with different internal structures that may be made by the system of FIG. 1.

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

Figure 1:
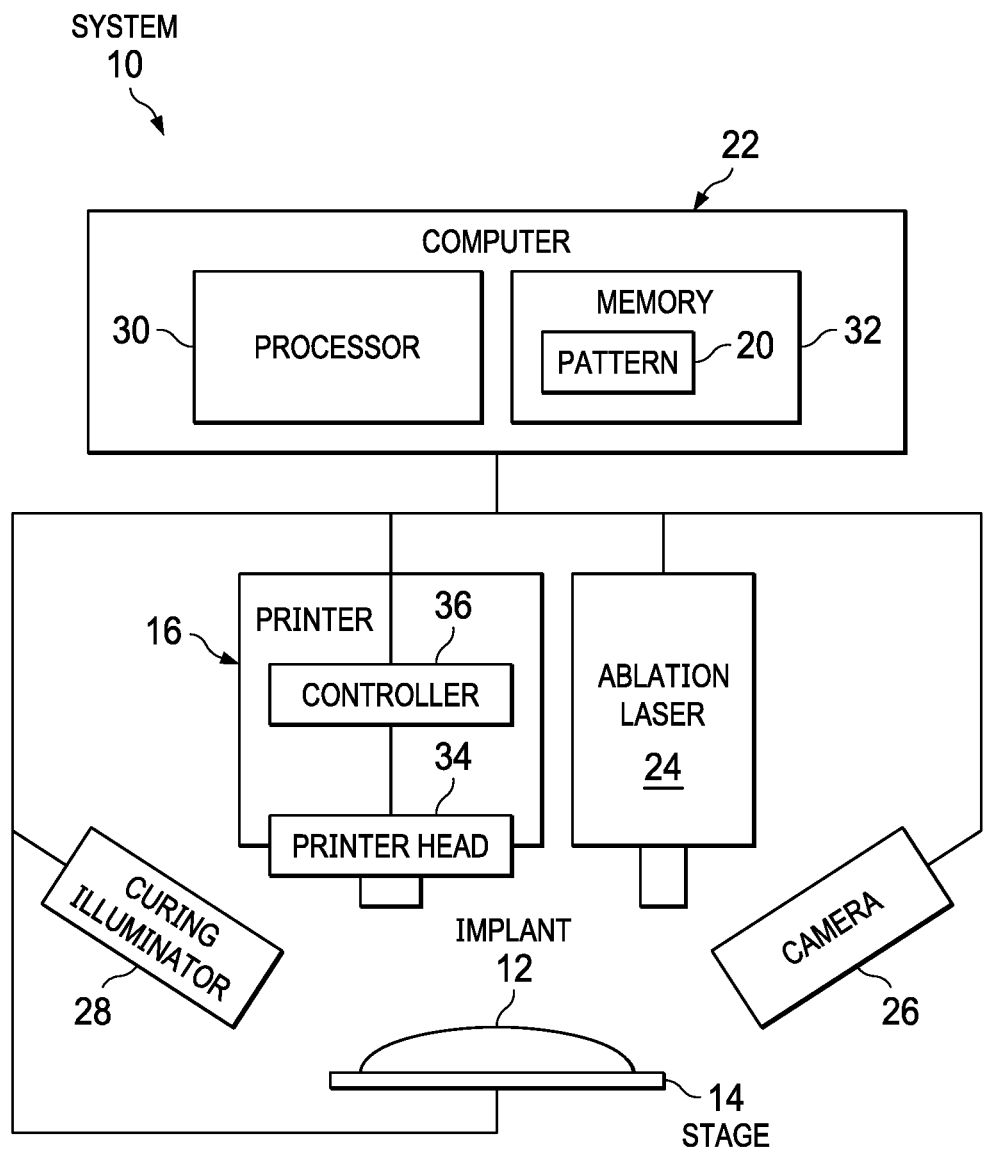
FIG. 1 illustrates an example of a system for making an implant for an eye.

FIG. 1 illustrates an example of a system 10 for making an implant 12 for an eye. System 10 includes a printer 16 that prints biological or biocompatible material onto a target, such as a stage 14. A computer 22 sends instructions to printer 16 to print the material according to a pattern 20. Pattern 20 is designed to yield implant 12 that provides refractive treatment to an eye when implanted into the eye. A camera 26 generates images to monitor the printing of the material. Computer 22 assesses the images according to pattern 20 and may adjust the instructions in response to the image. In certain embodiments, an ablation laser may shape the printed material, and a curing illuminator 28 may cure the printed material.

In the illustrated embodiment, system 10 comprises computer 22, printer 16, stage 14, ablation laser 24, camera 26, and curing illuminator 28. Computer 22 includes one or more processors 30 and one or more memories 32 that store pattern 20. Printer 16 includes a printer head 34 and a printer controller 36. As an overview, in certain embodiments, computer 22 controls the components of system 10 to make implant 12 according to pattern 20. Stage 14 is a platform that operates as either a target for printed material or a supports the target for the printed material. Printer 16 prints material onto the target. Ablation laser 24 ablates the printed material to shape the printed material according to pattern 20. Curing illuminator 28 illuminates the printed material with a light that promotes curing of the material. Camera 26 generates images to monitor the creation of implant 12. To aid in description, this description refers a coordinate system used in printing. In this coordinate system, the direction in which the printed material is ejected defines the z-axis, and the xy-plane is the plane normal to the z-axis.

Implant 12 is an ocular implant, i.e., an artificial aid surgically implanted into an eye to provide refractive treatment for the eye. When implant 12 is implanted into an eye and the eye recovers from the implantation, implant 12 changes the refractive properties of the eye to improve vision. Examples of implant 12 include a corneal inlay, corneal onlay, intraocular lens, or corneal transplant. In the case of a corneal transplant, system 10 creates "donor" tissue that may include cell layers like epithelial, Bowman, stromal, and/or endothelial cells. Donor tissue may be created for a full thickness cornea transplant (i.e., a penetrating keratoplasty) or a back layer cornea transplant (i.e., an endothelial keratoplasty).

Implant 12 may have any suitable size or shape. For example, implant 12 may be circular or annular with a diameter in the range of 0.5 to 12 millimeters (mm), or in a sub-range such as 0.5 to 5 mm, 5 mm to 8 mm, or 8 to 12 mm. In certain embodiments, implant 12 may comprise material printed on a transparent biocompatible substrate. (Examples of such printed material are described below.) In other embodiments, implant 12 may comprise the printed material, but not a substrate. An effective area of an implant 12 may be the area through which the eye sees, e.g., the area circumscribed by the pupil at its largest size.

Pattern 20 describes the external size and shape of implant 20 and may also describe internal structures of implant 20. Internal structures may result from how printed material is deposited, cured, and/or ablated during creation of implant 20. In certain embodiments, pattern 20 may define how material should be deposited, cured, and/or ablated at each layer that forms implant 20. For example, pattern 20 may define how a first layer should be made by describing where material should be deposited, whether and how the material should be cured, and/or whether and how the material should be ablated. Pattern 20 may define how subsequent layers should be made using a similar type of description. Examples of implants 12, internal structures, and patterns 20 are illustrated in FIGS. 3A to 4C.

Printer 16 may be any suitable printer configured to deposit material onto a target according to digital instructions. For example, printer 16 may be a 3D (or additive manufacturing) printer that deposits successive layers of material to yield printed material configured in a specific shape and size. Printer 16 includes printer head 44 and printer controller 46. Printer head 44 directs material onto the target and may be any suitable printer extruder that deposits material onto a surface. Printer controller 46 moves the printer head in the x, y, z directions to direct the material onto a specific location of the target, and may receive instructions from computer 22 to move the printer head 44 according to pattern 20.

Printer 16 prints material that comprises any suitable transparent or semitransparent material that is biological and/or biocompatible. Examples of such material include cultivated collagen material, human or animal cell material, biocompatible plastic, hyaluronan, recombinant human collagen III (RHCIII), gelatin methacrylate, and silk. In certain cases, a material over which the epithelium can grow may be used. Such material may provide optimal nutrition of corneal cells and extra-cellular material, optical transparency over lifetime, and supportive surface properties for epithelium growth.

Printer 16 prints material onto a target, which may be stage 14 or an implant substrate supported by stage 14. In certain embodiments, an implant substrate may be a mold that shapes the surface of material that is deposited on the mold. The mold may be removed prior to implantation of implant 12 into an eye. In other embodiments, an implant substrate may form a part of implant 20, and is implanted into an eye with the rest of the implant 20. In these embodiments, the implant substrate may comprise a transparent or semitransparent material that is biological and/or biocompatible, as described above.

Ablation laser 24 ablates printed material to shape the material according to pattern 20. Ablation laser 24 may be any suitable laser device that generates and emits a laser beam that ablates the printed material. Ablation laser 24 may comprise a laser source (e.g., excimer or femto) that generates a laser beam, and scanning components (e.g., optics) that direct the focus of the laser beam to specific points of the target. In certain embodiments, laser 24 may incorporate additional laser sources that generate different laser beams, e.g., laser 24 may have sources that generate a beam that photodisrupts or crosslinks the printed material and a beam that ablates the printed material. Computer 22 may instruct ablation laser 24 to shape the material by describing where the material should be ablated.

Curing illuminator 28 direct a curing light towards the printed material to cure the material. The light may cure the material by promoting cross-linking of the material. Examples of curing light include ultraviolet light or light (such as LED light) between 400 to 500 nm. Computer 22 may instruct curing illuminator 28 to cure material by indicating when the material should be cured, the curing time, and/or the curing intensity.

Camera 26 generates images of the printed material to monitor the printing of the material. Camera 26 may comprise any suitable system that can generate an image of an object. An optical coherence tomography (OCT) system (such as a time domain or frequency domain OCT system) that generates OCT scans to generate the image is an example of camera 26. Other examples include a Scheimpflug system (light section measurement) or a stereoscopic camera system.

Computer 22 sends instructions to the components of system 10 to tell the components how to operate to make implant 12 according to pattern 20. For example, computer 22 send instructions to printer controller 36 to move printer head 34 to print the material according to pattern 20. In certain embodiments, computer 22 can also send instructions to ablation laser 24 to ablate the printed material according to pattern 20, and/or to curing illuminator 28 to direct the curing light according to pattern 20.

In addition, computer 22 assesses images from camera 26 and can adjust the instructions in response to the image. Computer 22 may assess the image according to pattern 20 by comparing the image to pattern 20 to determine differences between the image and pattern 20. Computer 22 may image process the image to identify features of the image that correspond to the same features of implant 12 defined by pattern 20. The features may be, e.g., an external shape or size or an internal structure. The corresponding features are compared to detect any differences. If a difference is detected, the instructions may be adjusted to reduce the difference. For example, if the image shows material where pattern 20 indicates there should be no material, computer 22 may send instructions to ablation laser 24 to ablate the unwanted material. As another example, if the image shows no material where pattern 20 indicates there should be material, computer 22 may send instructions to printer 16 to deposit more material.

Computer 22 may perform the assessment and adjustment at any suitable time during the creation of implant 12. For example, computer 22 may continually perform the assessment and adjustment, or may perform the assessment and adjustment at certain times, e.g., after forming a layer and before forming a new layer.

Figure 2:
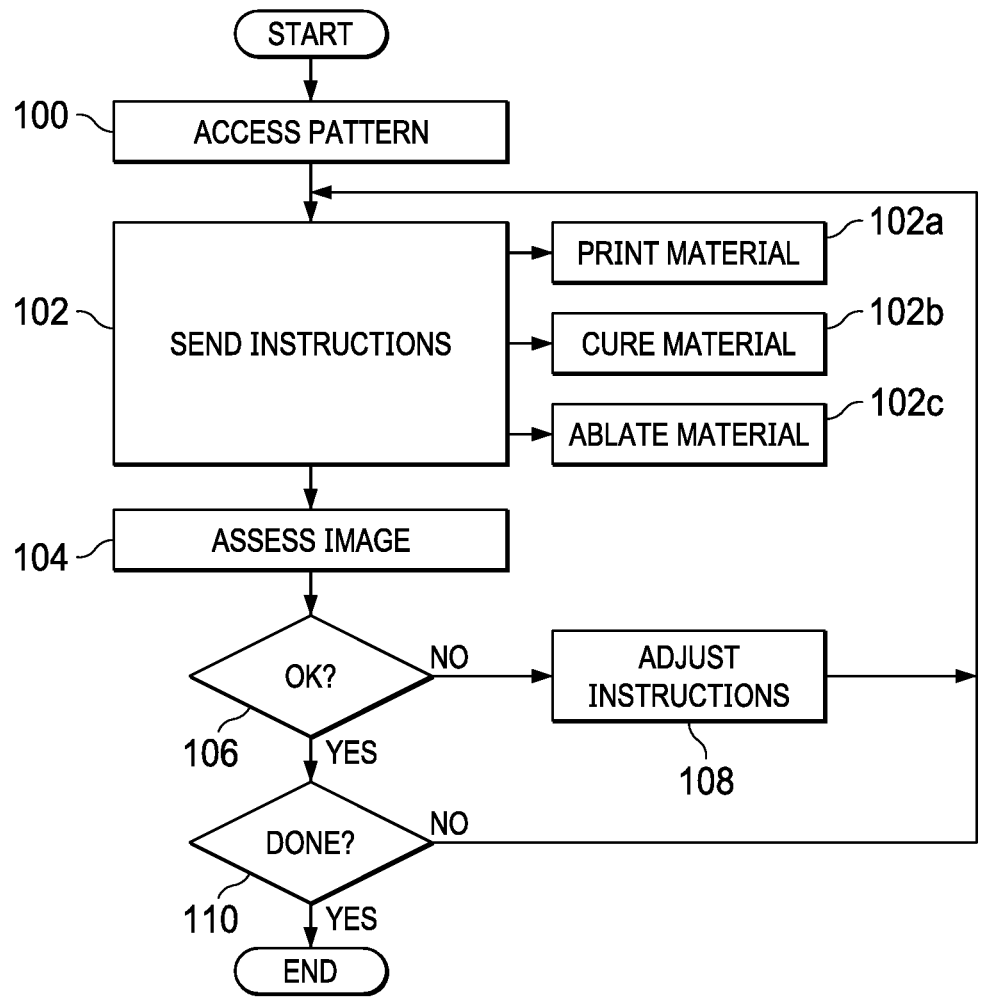
FIG. 2 illustrates an example of a method for making an implant for an eye, which may be performed by the system of FIG. 1.

FIG. 2 illustrates an example of a method for making an implant 12 for an eye, which may be performed by system 10 of FIG. 1. The method starts at step 100, where computer 22 accesses pattern 20 for making ocular implant 12. Computer 22 sends instructions to components of system 10 at step 102 to tell the components how to operate to make implant 12 according to pattern 20. For example, computer 22 sends instructions to: printer 16 at step 102a to print material according to pattern 20; curing illuminator 28 at step 102b to direct the curing light towards the printed material according to pattern 20; and/or ablation laser 24 at step 102c to ablate the printed material according to pattern 20.

Camera 26 generates images of the printed material, and computer 22 assesses the images at step 104. Computer 22 may assess the image according to pattern 20 by comparing the image to pattern 20 to determine differences between a feature (e.g., an external shape or size or an internal structure) of the image and a corresponding feature defined by pattern 20. Computer 22 determines if the printed material is satisfactory at step 106. The printed material may be satisfactory if there are no differences or only negligible between the features. A negligible difference may be a difference that causes no noticeable difference in the resulting vision.

If the printed material is not satisfactory at step 106, the method proceeds to step 108, where computer 22 adjusts the instructions in response to the image. The instructions may be adjusted to reduce the difference between the imaged feature and the pattern feature. For example, instructions may be adjusted to remove unwanted material or deposit needed material. In the first case, the instructions may instruct ablation laser 24 to ablate unwanted material. In the second case, the instructions may instruct printer 16 to print needed material.

If the printed material is satisfactory at step 106, the method proceeds to step 110, where computer 22 determines if the implant forming process is finished. If the process is not finished, the method returns to step 102 to send more instructions. If the process is finished, the method ends.

Figure 3A:
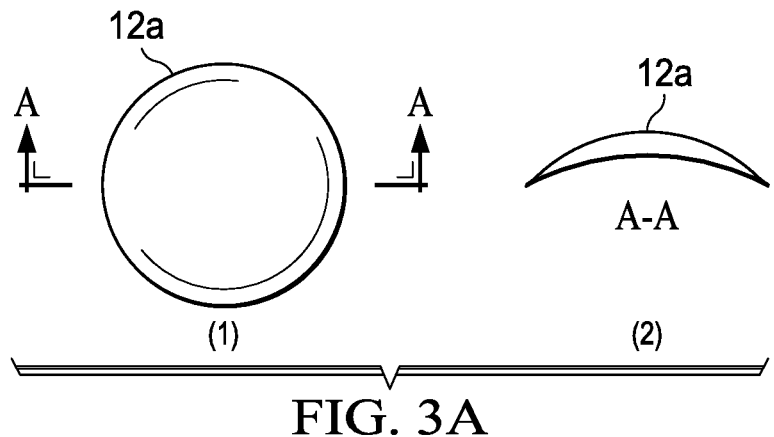
FIGS. 3A and 3B illustrate examples of implants with different external shapes that may be made by the system of FIG. 1.
Figure 3B:
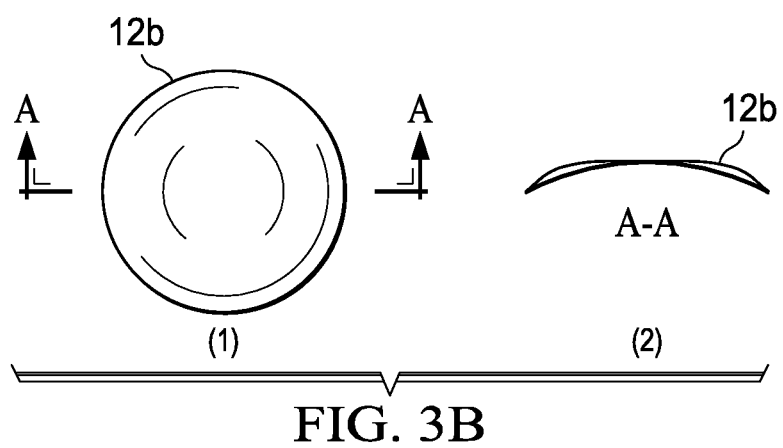

FIGS. 3A and 3B illustrate examples of implants 12 with different external shapes that may be made by system 10 of FIG. 1. Implant 12a of FIG. 3A may be used for correction of hyperopia, and implant 12b of FIG. 3B may be used for correction of myopia. FIGS. 3A(1) and 3B(1) illustrate a top view of implants 12a and 12b, respectively, and FIGS. 3A(2) and 3B(2) illustrate a cross-section view of implants 12a and 12b, respectively, along line A-A.

FIGS. 4A to 4C illustrate examples of implants 12c to 12e with different internal structures that may be made by system 10 of FIG. 1. Implants 12c to 12e are made by depositing layers 50, which may be defined by the patterns for implants 12c to 12e. Each figure shows formation of layers 50 in the effective area of implant 12. In each figure: step (1) shows layer 50a deposited onto a target (which may be stage 14 or an implant substrate); step (2) shows layer 50b deposited onto layer 50a and/or the target; and step (3) shows layer 50c deposited onto layer 50b. As each layer 50 is deposited (and optionally cured and/or ablated), it forms an internal structure that can affect the refractive properties of implant 12.

FIG. 4A illustrates an implant 12c with layers 50, where each layer 50 has substantially the same thickness. Layer 50a has a uniform curvature, and subsequent layers 50b and 50c have similar uniform curvature. Steps (4a) and (4b) illustrate how implant 12c can be ablated in different ways to yield different types of refractive correction. Step (4a) illustrates layers 50 ablated to yield an external shape similar to that of implant 12a of FIG. 3A for correction of hyperopia. Step (4b) illustrates layers 50 ablated to yield an external shape similar to that of implant 12b of FIG. 3B for correction of myopia.

FIGS. 4B and 4C illustrate implants 12d and 12e with layers 50, where layer 50a does not have the same thickness over the effective area, so subsequent layers 50b and 50c do not have a curvature similar to that of layer 50a. In FIG. 4B, layer 50a is deposited in the central, but not peripheral, area of implant 12d. Subsequent layers 50b and 50c are deposited, which results in an external shape similar to that of implant 12a of FIG. 3A for correction of hyperopia. However, even though implant 12d and implant 12c of Step (4a) of FIG. 4A have similar external shapes, their internal structures are different.

In FIG. 4C, layer 50a is deposited in the peripheral, but not central, area of implant 12e. Subsequent layers 50b and 50c are deposited, which results in an external shape similar to that of implant 12b of FIG. 3B for correction of myopia. However, even though implant 12e and implant 12c of Step (4b) of FIG. 4A have similar external shapes, their internal structures are different.

A component (e.g., a computer) of the systems and apparatuses disclosed herein may include an interface, logic, and/or memory, any of which may include hardware and/or software. An interface can receive input to the component, provide output from the component, and/or process the input and/or output. Logic can perform the operations of the component, e.g., execute instructions to generate output from input. Logic may be a processor, such as one or more computers or one or more microprocessors. Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. A system for making an implant for an eye, comprising:
   a printer configured to print material onto a target, the printer comprising:
      a printer head configured to deposit the material onto the target; and
      a printer controller configured to move the printer head to deposit the material onto a specific location of the target;
   a camera configured to generate an image to monitor the printing of the material;
   a computer configured to:
      store a pattern for the implant, the implant designed to provide refractive treatment for the eye;
      send instructions to the printer controller to move the printer head to print the material onto the target according to the pattern;
      assess the image from the camera according to the pattern; and
      adjust the instructions in response to the image; and
   an ablation laser configured to shape the printed material wherein the computer is configured to send instructions to the ablation laser to ablate the printed material according to the pattern:
   wherein the implant is formed of multiple layers with at least one layer at least partially ablated to produce a refractive correction for the implant, wherein the target comprises a substrate that forms a part of the implant, and wherein the substrate comprises a biological or biocompatible material that is transparent or semitransparent.

2. The system of claim 1, the camera comprising an optical coherence tomography (OCT) system, a Scheimpflug system, or a stereoscopic camera system.

3. The system of claim 1:
   further comprising a curing illuminator configured to direct a curing light towards the printed material; and
   wherein the computer is configured to send instructions to the curing illuminator to direct the curing light according to the pattern.

4. The system of claim 1, wherein the computer is configured to assess the image from the camera according to the pattern by comparing the image to the pattern.

5. The system of claim 1, wherein the computer is configured to assess the image from the camera according to the pattern by:
- identifying an internal structure of the printed material in the image; and
- comparing the identified internal structure with an internal structure defined by the pattern.

6. The system of claim 1, wherein the computer is configured to assess the image from the camera according to the pattern by:
- identifying an external shape of the printed material in the image; and
- comparing the identified external shape with an external shape defined by the pattern.

7. The system of claim 1, wherein the computer is configured to adjust the instructions in response to the image by:
- instructing the ablation laser to ablate unwanted material.

8. The system of claim 1, wherein the computer is configured to adjust the instructions in response to the image by:
- instructing the printer to print needed material.

9. The system of claim 1, the material comprising a biological or biocompatible material.

10. The system of claim 1, the target comprising a stage or an implant substrate.

11. The system of claim 1 wherein the implant is selected from the group consisting of: a corneal inlay, a corneal onlay, an intraocular lens, and a corneal transplant.

12. The system of claim 1 wherein the multiple layers comprise: at least first, second and third layers of similar uniform curvature, the third layer ablated in a central region of the third layer so as to form an implant with a shape for correction of hyperopia.

13. The system of claim 1 wherein the multiple layers comprise: at least first, second and third layers of non-uniform curvature, wherein the non-uniform curvature of the second and third layers is similar to each other, and the non-uniform curvature of the second and third layers are different from the non-uniform curvature of the first layer.

* * * * *